(12) United States Patent
Choi et al.

(10) Patent No.: US 9,790,929 B2
(45) Date of Patent: Oct. 17, 2017

(54) SHAPE CHANGEABLE MATERIAL HAVING INHERENT SHAPES USING HIERARCHICAL STRUCTURE AND ELECTRODE HAVING SAME

(71) Applicant: KOREA INSTITUTE OF SCIENCE AND TECHNOLOGY, Seoul (KR)

(72) Inventors: Insuk Choi, Seoul (KR); Yigil Cho, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/126,822

(22) PCT Filed: Mar. 17, 2015

(86) PCT No.: PCT/KR2015/002570
§ 371 (c)(1),
(2) Date: Sep. 16, 2016

(87) PCT Pub. No.: WO2015/142030
PCT Pub. Date: Sep. 24, 2015

(65) Prior Publication Data
US 2017/0092389 A1    Mar. 30, 2017

(30) Foreign Application Priority Data
Mar. 18, 2014  (KR) .................. 10-2014-0031710

(51) Int. Cl.
*F03G 7/00*   (2006.01)
*H01B 5/14*   (2006.01)
(Continued)

(52) U.S. Cl.
CPC ............... *F03G 7/00* (2013.01); *H01B 1/02* (2013.01); *H01B 1/04* (2013.01); *H01B 1/124* (2013.01); *H01B 5/14* (2013.01)

(58) Field of Classification Search
None
See application file for complete search history.

(56) References Cited

U.S. PATENT DOCUMENTS 4,736,587 A * 4/1988 Suzuki .................. F03G 7/065
137/625.46
5,137,991 A * 8/1992 Epstein .............. C08G 73/0266
252/500
(Continued)

FOREIGN PATENT DOCUMENTS

KR  10-2010-0123755 A   11/2010
KR  10-2010-0135569 A   12/2010
(Continued)

OTHER PUBLICATIONS

International Search Report issued in counterpart International Application No. PCT/KR2015/002570.

*Primary Examiner* — Dimary Lopez Cruz
*Assistant Examiner* — Muhammed Azam
(74) *Attorney, Agent, or Firm* — NSIP Law

(57) ABSTRACT

A shape changeable material includes a hierarchical structure including a basic displacement unit that includes a basic separation structure and basic unit cells, and a higher level displacement unit located inside the basic unit cell and including higher level unit cells distinguished from each other by a higher level separation structure, in which a separation structure including the basic separation structure and the higher level separation structure includes joints connecting neighboring unit cells to each other. By further forming a coating layer having electric conductivity, a shape changeable electrode includes a supporter that includes a shape changeable material, and the electric conductive coating layer provided on the supporter.

11 Claims, 11 Drawing Sheets

(51) Int. Cl.
  *H01B 1/12* (2006.01)
  *H01B 1/04* (2006.01)
  *H01B 1/02* (2006.01)

(56) References Cited

U.S. PATENT DOCUMENTS

| | | | | |
|---|---|---|---|---|
| 5,184,438 A * | 2/1993 | Takeda | | E04F 15/02405 |
| | | | | 174/505 |
| 5,187,907 A * | 2/1993 | Takeda | | E04F 15/02405 |
| | | | | 174/486 |
| 5,563,466 A * | 10/1996 | Rennex | | H02N 1/006 |
| | | | | 310/309 |
| 5,828,001 A * | 10/1998 | Schilham | | H02G 3/285 |
| | | | | 174/485 |
| 6,171,610 B1 * | 1/2001 | Vacanti | | A61F 2/28 |
| | | | | 424/426 |
| 6,574,958 B1 * | 6/2003 | MacGregor | | F03G 7/065 |
| | | | | 374/E5.031 |
| 7,188,473 B1 * | 3/2007 | Asada | | H02N 11/006 |
| | | | | 310/306 |
| 8,389,862 B2 * | 3/2013 | Arora | | H05K 1/00 |
| | | | | 174/254 |
| 8,395,855 B2 * | 3/2013 | Topliss | | F03G 7/065 |
| | | | | 348/340 |
| 8,434,303 B2 * | 5/2013 | Honda | | F03G 7/065 |
| | | | | 310/306 |
| 8,441,749 B2 * | 5/2013 | Brown | | F03G 7/065 |
| | | | | 359/813 |
| 8,446,475 B2 * | 5/2013 | Topliss | | F03G 7/065 |
| | | | | 348/208.11 |
| 8,448,434 B2 * | 5/2013 | Honda | | F03G 7/065 |
| | | | | 359/824 |
| 8,557,727 B2 * | 10/2013 | Yin | | B01J 23/42 |
| | | | | 502/100 |
| 8,588,598 B2 * | 11/2013 | Topliss | | F03G 7/065 |
| | | | | 396/132 |
| 8,593,568 B2 * | 11/2013 | Topliss | | F03G 7/065 |
| | | | | 348/202 |
| 8,695,334 B2 * | 4/2014 | Lewis | | E21B 33/064 |
| | | | | 60/527 |
| 8,830,026 B2 * | 9/2014 | Mooney | | H01H 71/145 |
| | | | | 200/5 R |
| 8,852,079 B2 * | 10/2014 | Sandstrom | | A61B 17/0218 |
| | | | | 600/205 |
| 8,883,287 B2 * | 11/2014 | Boyce | | B29C 59/02 |
| | | | | 174/254 |
| 9,127,696 B2 * | 9/2015 | Kocurek | | E21B 33/0355 |
| 9,145,903 B2 * | 9/2015 | Lewis | | E21B 33/064 |
| 9,206,789 B2 * | 12/2015 | Foshansky | | F03G 7/065 |
| 9,267,493 B2 * | 2/2016 | Browne | | F03G 7/06 |
| 9,288,898 B2 * | 3/2016 | Lavery | | H05K 1/0283 |
| 9,479,699 B2 * | 10/2016 | Brown | | F03G 7/065 |
| 2001/0029401 A1 * | 10/2001 | Ishida | | A61F 2/08 |
| | | | | 623/66.1 |
| 2002/0102674 A1 * | 8/2002 | Anderson | | A61F 2/14 |
| | | | | 435/174 |
| 2004/0152149 A1 * | 8/2004 | Reid | | A61F 2/06 |
| | | | | 435/29 |
| 2007/0117109 A1 * | 5/2007 | Rothemund | | C12P 19/34 |
| | | | | 435/6.12 |
| 2007/0224172 A1 * | 9/2007 | Hendriks | | A61L 27/3817 |
| | | | | 424/93.7 |
| 2012/0061124 A1 * | 3/2012 | Cui | | B82Y 20/00 |
| | | | | 174/128.1 |
| 2013/0041235 A1 * | 2/2013 | Rogers | | A61B 5/6867 |
| | | | | 600/306 |
| 2013/0269336 A1 * | 10/2013 | O'Connell | | F03G 7/00 |
| | | | | 60/527 |
| 2015/0060117 A1 * | 3/2015 | Wu | | H01B 1/02 |
| | | | | 174/255 |
| 2015/0237711 A1 | 8/2015 | Rogers et al. | | |
| 2015/0298322 A1 * | 10/2015 | Morris | | B25J 7/00 |
| | | | | 294/86.4 |
| 2015/0373838 A1 * | 12/2015 | Sawada | | C09D 105/16 |
| | | | | 136/256 |
| 2016/0084237 A1 * | 3/2016 | Miyairi | | F03G 7/00 |
| | | | | 60/530 |
| 2016/0084238 A1 * | 3/2016 | Miyairi | | F03G 7/00 |
| | | | | 60/530 |
| 2016/0090970 A1 * | 3/2016 | Miyairi | | F03G 7/00 |
| | | | | 60/530 |
| 2017/0014776 A1 * | 1/2017 | Li | | B01D 67/0088 |

FOREIGN PATENT DOCUMENTS

| | | |
|---|---|---|
| KR | 10-2013-0046100 A | 5/2013 |
| KR | 10-2013-0110659 A | 10/2013 |
| WO | WO 2013/147389 A1 | 10/2013 |

* cited by examiner

SHAPE CHANGEABLE MATERIAL HAVING INHERENT SHAPES USING HIERARCHICAL STRUCTURE AND ELECTRODE HAVING SAME

CROSS-REFERENCE TO RELATED APPLICATIONS

This application is a national stage application of International Application No. PCT/KR2015/002570 filed on Mar. 17, 2015, which claims the benefit of Korean Patent Application No. 10-2014-0031710 filed on Mar. 18, 2014, in the Korean Intellectual Property Office, the entire disclosures of which are incorporated herein by reference for all purposes.

BACKGROUND

1. Field

The present disclosure relates to a shape changeable material having inherent shapes using a hierarchical structure, and an electrode having the shape changeable material, and to a shape changeable material, wherein a plurality of unit cells having changeable relative locations are connected to each other and a shape of the shape changeable material may be changed to inherent shapes according to relative location change (displacement) of the unit cells, and an electrode manufactured by using the shape changeable material.

2. Description of Related Art

Most materials have a unique shape which is optimized for properties and functions of the materials. However, some materials may lose some functions by a specific stimulus, and external shapes thereof may be deformed.

When structural and morphological characteristics of a material are changed by a specific stimulus, such as external force or temperature, such changes are determined to be mechanical instability in general mechanical viewpoints, and thus may be considered as malfunction. However, inventors of the present disclosure thought such changes may be used to suggest a new type of material.

For example, a new material, such as a shape memory alloy, remembers an original shape even when it is deformed by applying force thereto, and thus has a characteristic of returning to the original shape when heat having a certain temperature or higher is applied thereto. Specifically, when a condition of a predetermined temperature or higher is satisfied, a shape of the material itself is changed while an arrangement of embedded crystals of the material is changed. In mechanical viewpoints, such a shape memory alloy may be evaluated as an unstable material that fails to maintain a standardized shape under a certain environment, but when such characteristics are used, the shape memory alloy is used in various fields, such as artificial organs, medical devices such as a bone-setting plate for orthopedics, and fire alarms.

Stem cells are undifferentiated cells having an ability to be differentiated into various body tissues. Moreover, stem cells have so-called pluripotency characteristics that the stem cells may be grown into any organ in a human body when a predetermined condition is satisfied. Meanwhile, while various electronic devices, such as a computer, a mobile phone, and a television, are repeatedly developed, devices used in an electronic product, such as a display device or an energy device, are improved in performance and thinned. Recently, efforts to not only manufacture devices which just are thin and have high performance, but also to implement characteristics, such as ductility, flexibility, and stretchability, which are difficult to implement using general devices, are continuously conducted.

The inventors of the present disclosure completed the present disclosure thinking that when a material changeable according to an external stimulus, such as a pluripotency, is manufactured and an electronic device is manufactured by using the material, it would become possible to manufacture a material that not only has flexibility or stretchability of an electronic device that is already studied, but also is changed to a pre-designed size or external shape as occasion demands, such as stem cells in a biomedical fields.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a shape changeable material includes a hierarchical structure including a basic displacement unit that includes a basic separation structure and basic unit cells, and a higher level displacement unit located inside the basic unit cell and including higher level unit cells distinguished from each other by a higher level separation structure, in which a separation structure including the basic separation structure and the higher level separation structure includes joints connecting neighboring unit cells to each other, in which the joints have a joint pattern in which a joint shape of an outer joint contacting an outer portion of a displacement unit and an inner joint not contacting the outer portion of the displacement unit is alternately repeated, and inherent shapes resulting from hierarchical joint patterns included in higher level displacement units and the hierarchical structure, and activated by rotation movement of the basic unit cells and the higher level unit cells and relative location changes between the unit cells.

In another general aspect, a shape changeable electrode includes a supporter that is a shape changeable material as described above, and an electric conductive coating layer provided on the supporter.

Other features and aspects will be apparent from the following detailed description, the drawings, and the claims.

DETAILED DESCRIPTION

Figure 1:
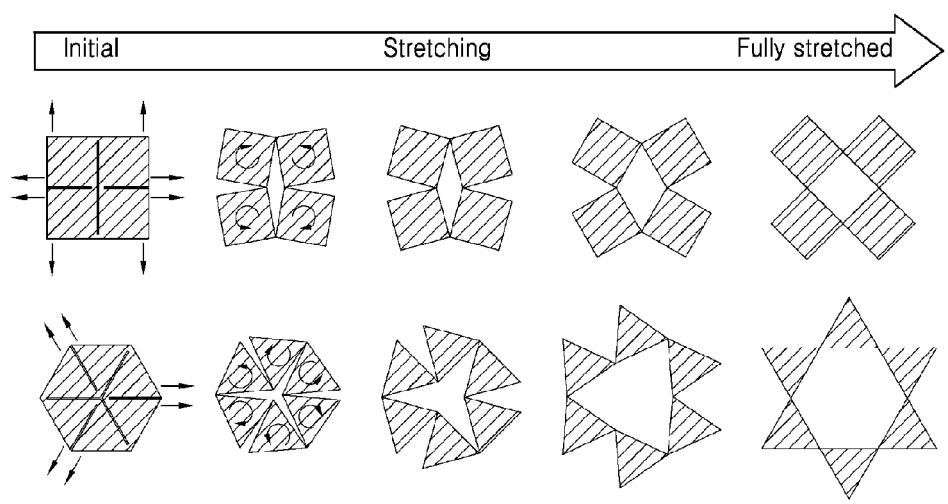
FIG. 1 is a schematic view for describing rotation movements each of unit cells undergo when a shape changeable material having inherent shapes is in an active state due to stretching, according to an embodiment of the present disclosure.

Hereinafter, one or more embodiments of the present disclosure will now be described more fully with reference to the accompanying drawings. However, the one or more embodiments of the present disclosure may be embodied in many different forms, and should not be construed as being limited to the embodiments set forth herein. Like reference numerals in the drawings denote like or similar elements throughout the specification. It will be understood by those of ordinary skill in the art that various changes in form and details may be made therein without departing from the spirit and scope as defined by the claims.

The present disclosure provides an embodiment of an electrode having inherent shapes by developing a material having 2-dimensional (2D) morphological pluripotency and applying the material to the electrode. An embodiment of a shape changeable material having a displacement unit structure, in which neighboring unit cells are connected to each other by a connecting part but relative locations of the unit cells are changeable, and having an external shape changeable to inherent shapes according to relative location change of the unit cells as the displacement unit structure is hierarchically formed, and an embodiment of an electrode manufactured by using the shape changeable material will be described below.

According to an aspect of the present disclosure, there is provided a shape changeable material having: a hierarchical structure including a basic displacement unit comprising a basic separation structure and a basic unit cell structure, and a higher level displacement unit located inside the basic displacement units and including a higher level separation structure and a higher level unit cell structure that are formed to have a repetitive pattern by the higher level separation structure; wherein a separation structure including the basic separation structure and the higher level separation structure includes joints connecting neighboring unit cells to each other, wherein the joints have a joint pattern in which a joint shape of an outer joint contacting an outer portion of a displacement unit and an inner joint not contacting the outer portion of the displacement unit is alternately repeated; and inherent shapes resulting from hierarchical joint patterns included in the basic displacement units and the higher level displacement units, and the hierarchical structure, and activated by rotation movement of the basic unit cells and the higher level unit cells and relative location changes between the unit cells.

A (primary) displacement unit to ($n^{th}$) order displacement unit may each include a separation structure having the joint pattern, and displacement units of consecutive orders may have an $n^{th}$ order hierarchical structure forming a hierarchical structure, wherein n is an integer equal to or higher than 2.

The (primary) displacement unit may have a (primary) unit cell structure including a (primary) unit $cell_1$ to a (primary) unit $cell_m$ that are m (primary) unit cells distinguished from each other by a (primary) separation structure, wherein m is an integer of 4 or 6; the (primary) separation structure may include a (primary) separation $part_1$ to a (primary) separation $part_m$ that are m (primary) separation parts separating neighboring (primary) unit cells from each other, and include a (primary) $joint_1$ to a (primary) $joint_m$ that are m (primary) joints provided at one end of each of the (primary) separation parts, connecting neighboring (primary) unit cells to each other, and having the joint pattern, and at least one (primary) unit cell from among the m (primary) unit cells may have, as a (secondary) displacement unit, a secondary or more hierarchical structure including a (secondary) separation structure having a same separation structure as the (primary) separation structure, and a (secondary) unit cell structure having the same separation structure as the (primary) separation structure.

The shape changeable material may have an $(n^{th})$ order hierarchical structure including a (primary) displacement unit to an $(n^{th})$ order displacement unit, wherein n is an integer equal to or higher than 3, wherein the (primary) separation structure may have an alpha-type joint pattern in which the (primary) joint$_1$ to the (primary) joint$_m$ each have a joint shape selected from an outer joint and an inner joint, and neighboring joints in the (primary) separation structure have different joint shapes, The (secondary) separation structure may have any one joint shape selected from an alpha-type joint pattern in which the (secondary) joint$_1$ to the (secondary) joint$_m$ have same joint shapes as the (primary) joint$_1$ to the (primary) joint$_m$, and a beta-type joint pattern in which the (secondary) joint$_1$ to the (secondary) joint$_m$ have different joint shapes from the (primary) joint$_1$ to the (primary) joint$_m$. Also, a (tertiary) separation structure or each of (tertiary) separation structure to $(n^{th})$ order separation structure has any one joint pattern selected from the alpha-type joint pattern and the beta-type joint pattern.

The (primary) displacement unit to $(n^{th})$ displacement unit may each have a quadrangular outer line, wherein m is 4. The quadrangle is not limited as long as it is a tetragon, and any one of various quadrangles may be applied, such as a square and a rectangle.

The unit cells and the joints may include any one material selected from the group consisting of silicon rubber, polyester resin, hydrogel, a transition metal, carbon fiber, and a combination thereof, and may be formed of any one of the materials.

Each of the joints connecting the neighboring unit cells may form a hinge structure.

According to another aspect of the present disclosure, there is provided a shape changeable electrode including: a supporter that is the shape changeable material; and an electric conductive coating layer provided on the supporter.

The electric conductive coating layer may include any one selected from the group consisting of an electric conductive metal nano-particle, carbon nano-tube, graphene, electric conductive polymer, and a combination thereof.

As the disclosure allows for various changes and numerous embodiments, particular embodiments will be illustrated in the drawings and described in detail in the written description. However, this is not intended to limit the present disclosure to particular modes of practice, and it will to be appreciated that all changes, equivalents, and substitutes that do not depart from the spirit and technical scope of the present disclosure are encompassed in the present disclosure. The terms "first" "second", "(primary)", "(secondary)", etc. are used to describe various elements, but the elements are not limited by such terms. The terms are used only to distinguish one element from another element. For example, a first element may be terms a second element and similarly, a second element may be termed a first element without departing from the teachings of this disclosure.

In addition, the term "include", "have", or "comprise" is intended to indicate the presence of a characteristic, number, step, operation, element, part, or any combination thereof described in the specification, and should be understood that the presence or addition possibility of one or more other characteristics or numbers, steps, operations, elements, parts, or any combination thereof is not pre-excluded.

Hereinafter, unless specifically mentioned, a case where a distance between unit cells increases and thus the unit cells have an inherent shape will be referred to as an active state, and a case where the distance between the unit cells is minimal will be referred to as a latent state. Also, unless specifically mentioned, so-called displacement or transformation means a 2-dimensional (2D) change of a shape of a material, i.e., a change of an area of the material.

Hereinafter, in order to exhibit elements (a separation structure, a unit cell, a displacement unit, and the like) constituting the same dimension in the hierarchical structure, the terms such as basic, higher level, (primary), and $(n^{th})$ order will be together used. Further, when elements of different dimensions are all referred to or when a general characteristic of an element is described, a title of each element is used.

The shape changeable material may be in a form of a sheet, in a form of a substrate having a uniform thickness in a single layer, or in a form in which a multilayer of films are stacked on each other. Also, unless specifically mentioned, a type of a material forming the shape changeable material is not specifically limited as long as the material has characteristics of the shape changeable material.

The present disclosure will be described in detail.

A shape changeable material according to an embodiment of the present disclosure has inherent shapes induced by a hierarchical changeable units and a predetermined joint pattern formed in each of the changeable units. Also, the shape changeable material may be in an active state or a latent state (inherent state) depending on relative location (or distance) changes between unit cells. In detail, an overall external shape of the shape changeable material may change according to a rotation movement of two unit cells connected to each other based on one joint being separated from each other or approaching each other, and relative location movements between a plurality of unit cells deriving from each rotation movement of the unit cells. Hereinafter, a case where an inner area of a line connecting an outer portion of the shape changeable material is minimum is referred to as a latent state, and a case where an inner area of the line connecting the outer portion of the shape changeable material is larger than the inner area in the latent state is referred to as an active state.

The shape changeable material includes a displacement unit including a separation structure and a unit cell structure, and unit cells included in the unit cell structure again have, as displacement units in another dimension, a hierarchical structure in which a structure including a separation structure and a unit cell structure is repetitively formed.

When the displacement units are hierarchically formed while having different dimensions as such, the displacement units appear to have a tile pattern as a predetermined pattern is repeatedly formed on a surface of the shape changeable material in the latent state.

The shape changeable material may have a 2-dimensional (2D) hierarchical structure of a basic dimension and a higher level dimension by including a basic displacement unit including a basic separation structure and a basic unit cell structure, and a higher level displacement unit formed in each of the basic displacement units and including a higher level separation structure and a higher level unit cell structure, which are formed to have a repetitive pattern by the higher level separation structure.

FIG. 1 is a schematic view for describing cases where a shape changeable material according to an embodiment of the present disclosure is in a latent (inherent) state and in an active state according to stretching, and rotation and movement of each unit cell during such processes. For convenience of description, a hierarchical structure is not formed in FIG. 1, and only a displacement unit in the same dimension is shown.

According to an embodiment, a basic structure of a displacement unit, a process of the displacement unit changing to an active state, and a configuration principle of the displacement unit will be described based on a displacement unit having a quadrangular external shape at the top of FIG. 1.

The quadrangular displacement unit includes four unit cells that are separated from each other by a separation structure including four separation parts therein and joints formed at one end of each of the separation parts. The unit cells will be referred to as unit cell$_1$ to unit cell$_4$ in an order from a left top unit cell in a clockwise direction, a separation part provided between the unit cell$_1$ and unit cell$_2$ will be referred to as a separation part$_1$, and a joint$_1$ that is a joint formed in a region where the separation part$_1$ and an outer line of the displacement unit meet has a shape of an outer joint. Also, a separation part$_2$ has a shape of an inner joint since it is provided inside the displacement unit that does not contact the outer line of the displacement unit.

The joint$_1$ to joint$_4$ have any one joint shape from among an outer joint and an inner joint, and are configured such that the outer joint and the inner joint are alternately repeated. This is a condition for rotating and moving the unit cells while the displacement unit changes to the active state, and means that two neighboring joints (joints in the same dimension and simultaneously contacting one unit cell) do not have the same shape of an outer joint or an inner joint. When force is applied in a direction indicated by an arrow of FIG. 1, each of the unit cells rotates in a direction displayed therein and thus the unit cells perform rotation movement of being separated from each other. According to the rotation movement, the separation structure has an empty space surrounded by the unit cells, and accordingly, an overall shape or size of the displacement unit changes.

According to an embodiment, a basic structure of a displacement unit and changes shown when the displacement unit changes to an active state based on a displacement unit having a hexagonal external shape at the bottom of FIG. 1 will be described. The hexagonal displacement unit includes six unit cells separated from each other by a separation structure including six separation parts therein and joints formed at one end of each of the separation parts. The joints connecting the neighboring unit cells alternately have shapes of an outer joint and an inner joint, and thus two joints contacting one unit cell have different joint shapes. When pulling forces are applied in directions indicated by arrows of FIG. 1 to the hexagonal displacement unit, each of the unit cells rotates in a direction indicated by a displayed arrow and changes to an active state, and when the unit cells are separated from each other as much as possible, the displacement unit may have a rightmost shape with an empty space surrounded by the unit cells.

In the displacement unit that does not have a hierarchical structure as shown in FIG. 1, inherent shapes do not show a difference by relative locations of the outer joint and the inner joint; however, in a shape changeable material having a secondary or more hierarchical structure, joints included in a displacement unit of each order and at corresponding locations are distinguished whether they have the same joint shape or different joint shapes, and a shape of the shape changeable material is different in an active state.

For example, when a (secondary) joint$_1$ to a (secondary) joint$_m$ connecting m (secondary) unit cells to each other have a joint shape in which an outer joint and an inner joint are each provided in the same direction and at locations corresponding to a (primary) joint$_1$ to a (primary) joint$_m$ connecting m (primary) unit cells to each other, a (primary) separation structure and a (secondary) separation structure both have an alpha-type joint pattern; and when they have different joint shapes, the (primary) separation structure has an alpha joint pattern and the (secondary) separation structure has a beta joint pattern.

Figure 2:
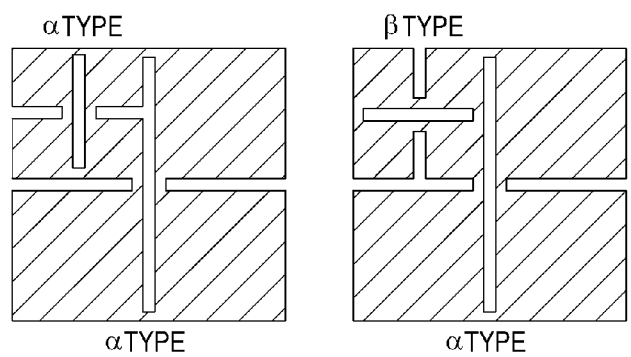
FIG. 2 is a conceptual view for describing a separation structure of a shape changeable material having a secondary hierarchical structure according to an embodiment of the present disclosure. The secondary hierarchical structure is a shape changeable material (left side) in which a (primary) separation structure of a material having inherent shapes is an alpha-type and corresponds to a left top unit cell from among primary unit cells, and a (secondary) separation structure formed in a (secondary) displacement unit operating as a (secondary) displacement unit is an alpha-type. A shape changeable material (right side) having the same example as that on the left side but a (secondary) separation structure is a beta-type.

FIG. 2 is a conceptual view for describing a separation structure of a shape changeable material having a secondary hierarchical structure according to an embodiment of the present disclosure. The secondary hierarchical structure is a shape changeable material (left side) in which a (primary) separation structure of a material having inherent shapes is an alpha-type and corresponds to a left top unit cell from among primary unit cells. A (secondary) separation structure formed in a (secondary) displacement unit operating as a (secondary) displacement unit is an alpha-type, and a shape changeable material (right side) having the same example as that on the left side but a (secondary) separation structure is a beta-type. Referring to FIG. 2, an overall shape of the separation structure of the shape changeable material having the secondary or higher hierarchical structure becomes different according to a difference of relative shapes of joints included in the (primary) separation structure and the (secondary) separation structure.

In detail, cases where joint patterns included in the (primary) displacement unit and the (secondary) displacement unit are the same and different from each other are distinguished from each other, and the shape changeable material having the secondary or higher hierarchical structure may be classified into at least two types of joint patterns depending on whether a joint shape included in each order is the same as or different from a joint shape of the (primary) separation structure, and may have an alpha-alpha type joint shape as shown in the left of FIG. 2 and an alpha-beta-type joint shape as shown in the right of FIG. 2.

The shape changeable material having such a joint shape may have further various types of joint shapes as an order of a hierarchical structure increases, and inherent shapes (an external shape in an active state) may be adjusted by changing the number of hierarchical structures and a type of a joint shape.

Also, when a condition in which a value obtained by multiplying an angle between neighboring separation parts and m that is the number of joints is 360 is satisfied, the shape changeable material may appear to be a plane in a latent state.

Figure 3:
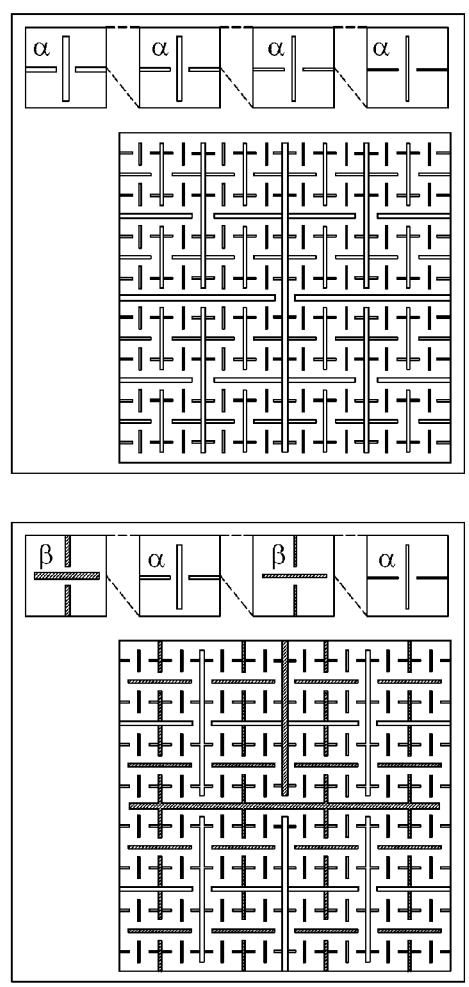
FIG. 3 illustrates an example in which a shape changeable material having inherent shapes, according to an embodiment of the present disclosure, has a quaternary hierarchical structure, wherein an upper example is a case where all of primary to quaternary hierarchical structures have an alpha-type separation structure, and a lower example is a case where primary to quaternary hierarchical structures are alternately a beta-type and an alpha-type.
Figure 4:
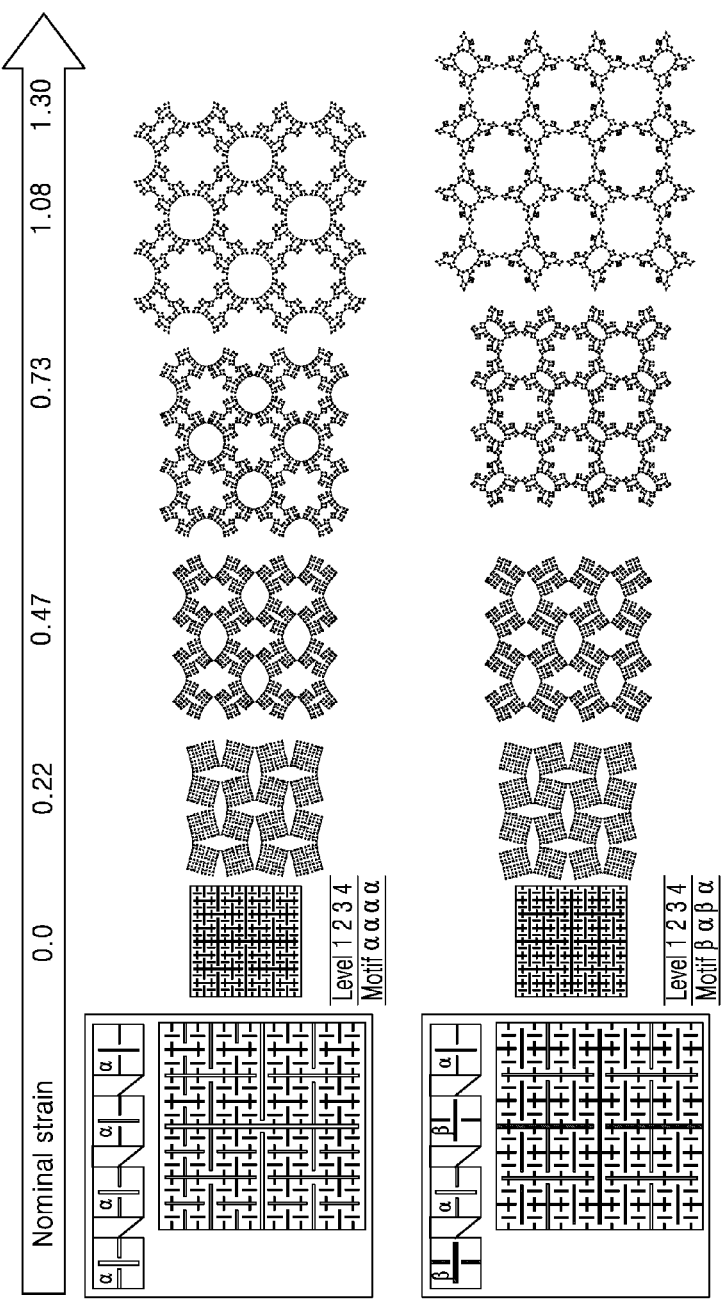
FIG. 4 illustrates an example in which a shape changeable material having inherent shapes, according to an embodiment of the present disclosure, has a quaternary hierarchical structure, wherein an upper example is a material where all of a primary to quaternary hierarchical structures have an alpha-type separation structure, a lower example is a material where primary to quaternary hierarchical structures sequentially repeatedly have alpha-type separation structure and a beta-type separation structure, and each of the materials is changed to an active state in a stepwise manner.

FIG. 3 illustrates an example in which a shape changeable material having inherent shapes, according to an embodiment of the present disclosure, has a quaternary hierarchical structure, wherein an upper example is a case where all of primary to quaternary hierarchical structures have an alpha-type separation structure, and a lower example is a case where primary to quaternary hierarchical structures are alternately a beta-type and an alpha-type. FIG. 4 illustrates processes in which, when a material having a latent shape according to an embodiment of the present disclosure has a quaternary hierarchical structure, the material changes from a latent state to an active state according to stretching.

Referring to the processes in which a shape changeable material changes to an active state as shown in FIG. 4, shapes are different in the active state when all dimensions have an alpha-type joint pattern (top) and when dimensions have beta, alpha, beta, and alpha-type joint patterns (bottom) in primary to quaternary displacement units. In other words, a shape changeable material having different shapes in an active state even when an external shape is the same in a latent state may be provided by changing an order of a hierarchical structure and a joint pattern of each order.

Hereinabove, unit cells of the same order included in a shape changeable material have the same internal structure, but if required, the unit cells of the same order may have different patterns or some of the unit cells may not include a separation structure. Also, even when an externals shape is almost the same in a latent state, shapes in an active state may vary according to such transformation.

Figure 5:
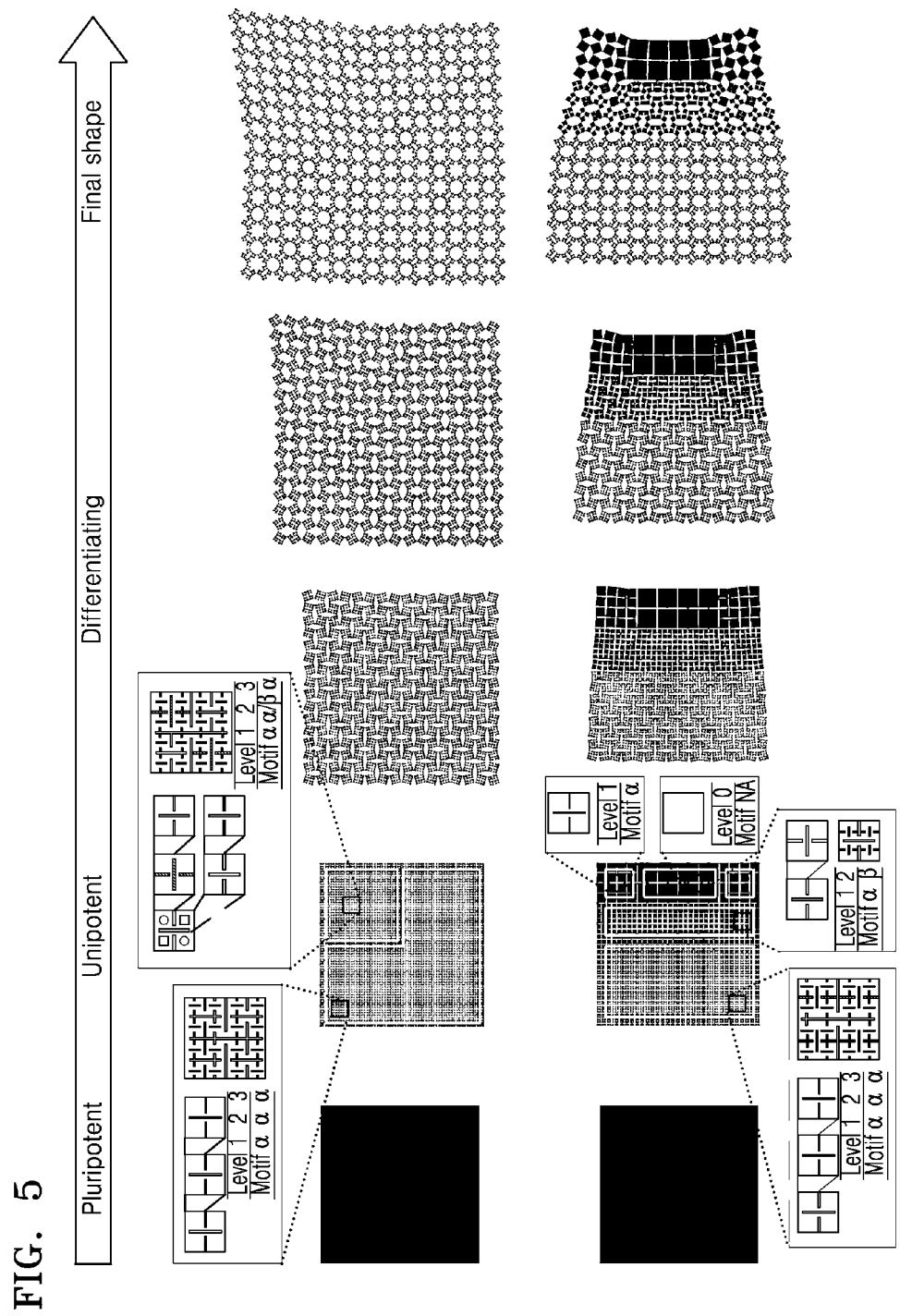
FIG. 5 illustrates an example in which a shape changeable material having inherent shapes, according to an embodiment of the present disclosure, has an octonary hierarchical structure, wherein upper and lower examples are examples in which shapes and areas are adjusted when a material having an octonary hierarchical structure is in an active state by adjusting a type of a separation structure with each order of a right top unit cell from among primary unit cells and other primary unit cells. The examples illustrate an example (the upper example) in which a tertiary unit cell, in which all of primary separation structure, a secondary separation structure, and a tertiary separation structures have an alpha-type separation structure, and tertiary unit cells having a separation structure, in which an alpha-type separation structure and a beta-type separation structure are each mixed and used in a secondary separation structure, are present together, or an example (the lower example) in which a zero-order unit cell that does not include an additional separation structure therein and tertiary unit cells, in which an alpha-type separation structure and a beta-type separation structure are sequentially shown, are present together.

FIG. 5 illustrates an example in which a shape changeable material having inherent shapes, according to an embodiment of the present disclosure, has a tertiary hierarchical structure, wherein upper and lower examples are examples in which shapes and areas are adjusted when a material having a tertiary hierarchical structure is in an active state by adjusting a type of a separation structure with each order of a right top unit cell from among primary unit cells and other primary unit cells.

The examples illustrate an example (the upper example) in which a tertiary unit cell, in which all of primary separation structure, a secondary separation structure, and a tertiary separation structures have an alpha-type separation structure, and tertiary unit cells having a separation structure, in which an alpha-type separation structure and a beta-type separation structure are each mixed and used in a secondary separation structure, are present together, or an example (the lower example) in which a zero-order unit cell that does not include an additional separation structure therein and tertiary unit cells, in which an alpha-type separation structure and a beta-type separation structure are sequentially shown, are present together.

Figure 6:
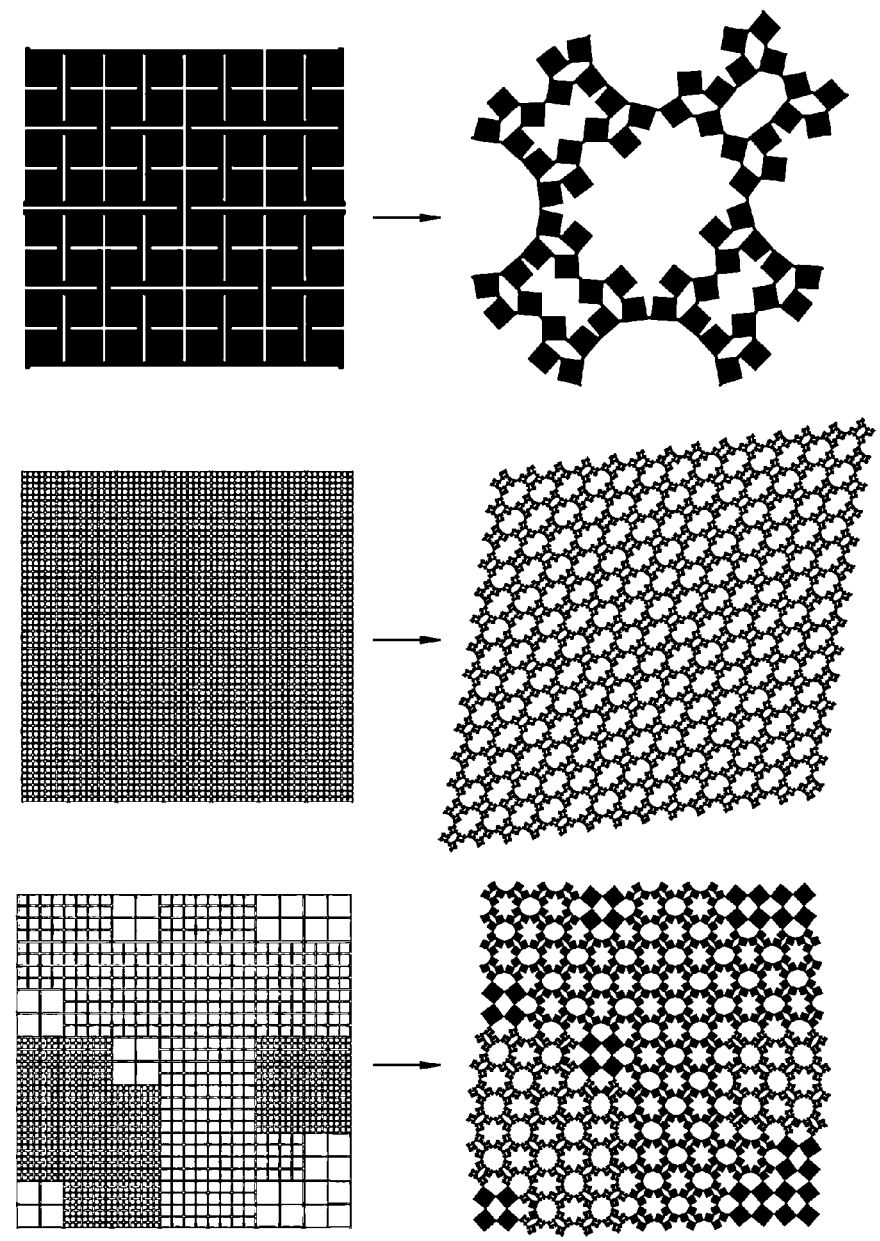
FIG. 6 illustrates examples of a shape changeable material having inherent shapes designed according to an embodiment of the present disclosure, wherein upper, middle, and lower examples illustrate that hierarchical structures have similar external shapes in a latent state but have different shapes and areas in an active state depending on orders of the hierarchical structures and a separation structure of each of the orders.

FIG. 6 illustrates examples of a shape changeable material having inherent shapes designed according to an embodiment of the present disclosure, wherein upper, middle, and lower examples illustrate that hierarchical structures have similar external shapes in a latent state but have different shapes and areas in an active state depending on orders of the hierarchical structures and a separation structure of each of the orders.

In other words, a shape changeable material having various shapes and areas (including an area between unit cells) may be provided depending on an order of the shape changeable material, whether a displacement of a higher level dimension is to be formed inside each unit cell, and a type of a joint pattern formed inside the shape changeable material of each order. Also, inherent shapes of the shape changeable material may be reversibly manifested, and may provide a material having a shape reversibly changing by manifesting a latent state according to a predetermined stimulus or manifesting an active state according to a predetermined stimulus.

The shape changeable material may include a single material or a mixture of various materials. When a material having fracture resistance of not being fractured even by rotation momentum applied to a joint, such as silicon rubber, is applied to the shape changeable material, the shape changeable material may be entirely manufactured by using the same material, and when not, the shape changeable material may be manufactured by using different materials while having a structure in which unit cells are connected to each other by a joint using mechanical connection, such as a hinge structure.

The shape changeable material may be manufactured by using a 3D printer after being designed to have a pre-specified hierarchical structure, and may be manufactured by manufacturing a mold of the shape changeable material having the pre-specified hierarchical structure by using a 3D printer and then molding polymer resin or the like by using the mold. Also, the shape changeable material may be manufactured by assembling unit cells having a pre-specified size and structure to a joint having a hinge structure or the like.

An electrode according to another embodiment of the present disclosure includes the shape changeable material as a supporter. A shape changeable electrode having inherent shapes may be manufactured via a simple method of forming an electric conductive coating layer on at least one surface of the shape changeable material by applying the shape changeable material as a supporter.

The coating layer may be formed by using a general method of forming an electric conductive coating layer, and in detail, may be formed by depositing an electric conductive metal, a carbon nano-material having electric conductivity, or the like on at least one surface of the shape changeable material, or by manufacturing an electric conductive coating solution and then coating the electric conductive coating solution on the shape changeable material.

In detail, the electrode may be manufactured by manufacturing the electric conductive coating solution by mixing with an electric conductive metal nano-particle, carbon nano-tube, electric conductive polymer such as graphene, or by mixing with polymer resin operating as a binder, and then forming a coating film by using the electric conductive coating solution, but a method of manufacturing the electrode is not limited thereto.

When the electrode is formed by using the shape changeable material as a supporter, a flexible characteristic and a stretchable characteristic may be assigned to the electrode. In other words, since the electrode that 2-dimensionally expands or is reduced according to characteristics of the shape changeable material is provided, the electrode having a stretchable characteristic may be provided. Also, a flexible characteristic may be assigned to the shape changeable electrode by adjusting characteristics of a connecting part connecting unit cells of the shape changeable material. In addition, since an electrode that is closely adhered not only on a regular curved surface but also on a curved surface of an irregular external shape without a lifting may be manufactured by adjusting sizes of unit cells included in the shape changeable material and an order of a hierarchical structure, utilization of the electrode is high in fields that require a surface-adhered electrode and in fields that require a flexible electrode.

EXAMPLES

Example 1: Manufacture of Shape Changeable Material Having Quaternary Hierarchical Structure by Using 3-Dimensional (3D) Printer A displacement unit including a separation structure in which (primary) to (quaternary) displacement units respectively have alpha-type, beta-type, alpha-type, and beta-type joint patterns was formed by using a 3D printer (Objet260 Connex™ from Stratasys Design Line).

Figure 7:
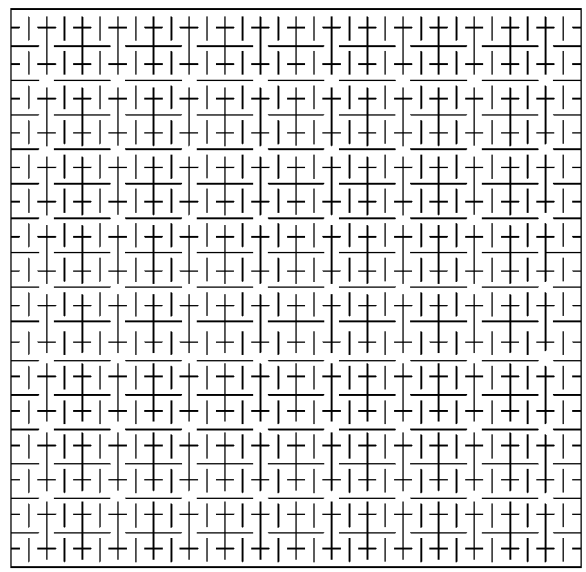
FIG. 7 illustrates an example of manufacturing a material having a tertiary hierarchical structure by using a 3-dimensional (3D) printer in Example 1, and a separation structure of the material is an actual photograph in a latent state of a sample in which all of primary to tertiary separation structures are an alpha-type separation structure.
Figure 8:
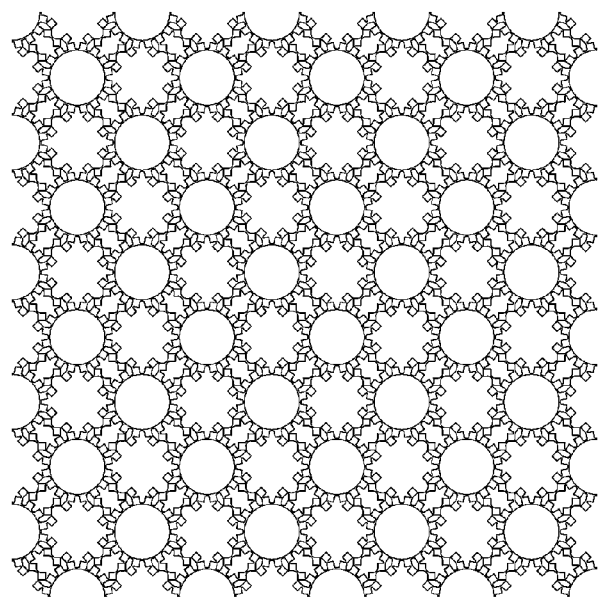
FIG. 8 is a photograph taken while the material of FIG. 7 is set in an active state.

FIG. 7 illustrates an example of manufacturing a material having a quaternary hierarchical structure by using a 3D printer in Example 1, and a separation structure of the material is an actual photograph in a latent state of a sample in which primary to quaternary separation structures alternately have alpha-type and beta-type separation structures, and FIG. 8 is a photograph taken while the material of FIG. 7 is set in an active state.

Referring to FIGS. 7 and 8, unit cells are transformed to an inherent shape of FIG. 8 as each of the unit cells is rotated and moved by a stimulus of external force.

Example 2: Manufacture of Shape Changeable Electrode

A mold capable of manufacturing a shape changeable material of Example 2 was manufactured by using the same 3D printer used in Example 1, and the shape changeable material of Example 2 formed of silicone rubber was manufactured by using the mold.

An electric conductive coating layer was formed on a surface of the shape changeable material of Example 2 by using following operations.

Operation 1: Carbon nano-tube gel was prepared as follows by mixing carbon nano-tubes (a product manufactured by Hanwha Nanotech Corporation) with an imidazolium-based ionic liquid.

20 mg of single-walled carbon nano-tubes were put into a mortar, and 20 mg or 60 mg of 1-butyl-3-methylimidazolium bis(trifluoromethylsulfonyl)imide was put into the mortar. Thereafter, a material in the form of gel was obtained by sufficiently stirring the mixture using a pestle for about 10 minutes.

Operation 2: The prepared carbon nano-tube gel was put into a vial containing 20 ml of toluene, and an ultrasonic treatment was performed by using a bath-type sonicator for 1 hour.

Operation 3: A commercially available silicone rubber KE-441 manufactured by Shinetsu Chemical Co. was dissolved in a carbon nano-tube solution prepared in Operation 2. At this time, the silicone rubber was put such that the content of silicone rubber is equal to a desired content ratio of the carbon nano-tubes. In other words, 480 mg of KE-441 was put in order to obtain a composite including 4 wt % of carbon nano-tubes. Next, the mixture was stirred at a speed of 1,500 rpm for about 6 hours. A mixture solution of carbon nano-tubes/polymer was coated on a substrate by using an air spray. For a coating method, a substrate composed of a shape changeable material was sufficiently pre-heated on a hot plate at 50° C. for 30 minutes, and then the mixture solution with a predetermined content was spray-coated thereon. The coated film was dried on the hot plate at 50° C. for about 1 hour, and then further dried in a vacuum oven overnight.

Operation 4: In order to dope the manufactured film with acid, a Petri dish containing 5 ml of nitric acid was placed on a hot plate preheated to 70° C., and the upper portion was covered by using a very wide beaker. After about 10 minutes, a film coated with a composite electrode was placed in the beaker by using a pair of laboratory pincers, and the beaker was again covered to allow the film to be exposed to a nitric acid vapor for about 30 minutes. After the acid vapor doping was completed, the film was dried in a vacuum oven overnight.

Figure 9:
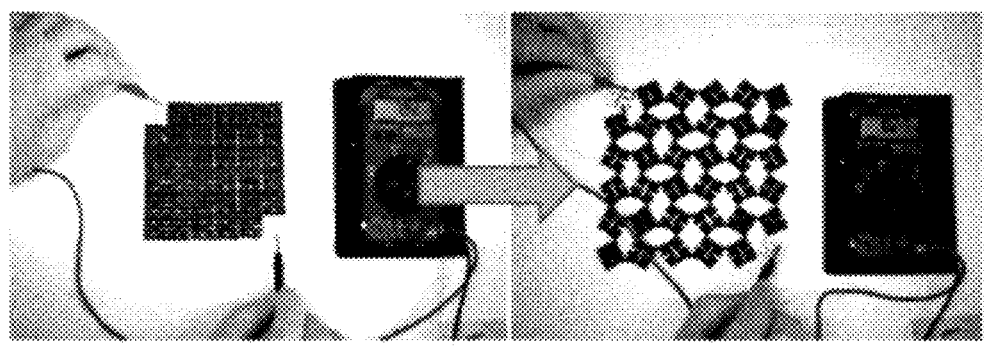
FIG. 9 is photographs of a shape changeable electrode in a latent state (left side) and an active state (right side), which is manufactured by adding an electric conductive coating layer to a shape changeable material having inherent shapes manufactured according to Example 2, to show that the shape changeable electrode maintains electric conductivity even in the active state.
Figure 9:
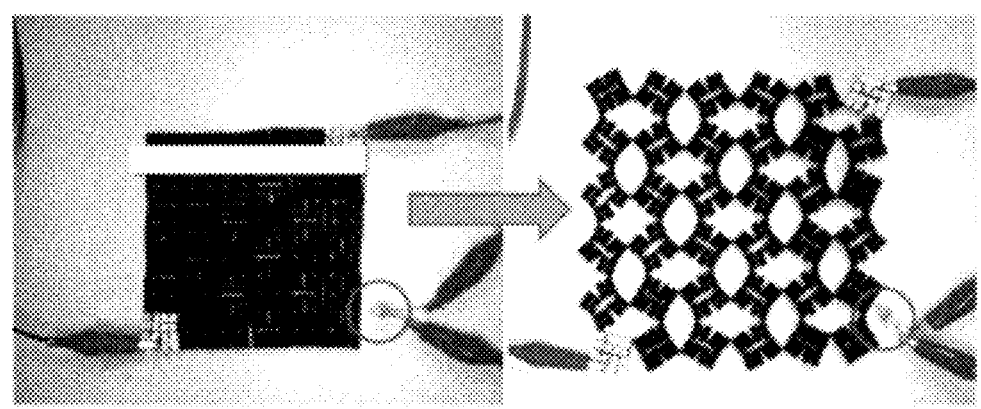

The electric conductivities of the shape changeable electrode manufactured in Example 2 in the latent state and the active state were compared to each other, and the results are shown in FIG. 9. Referring to FIG. 9, it is confirmed that the electric conductivities in both the latent state and the active state were maintained.

Figure 10:
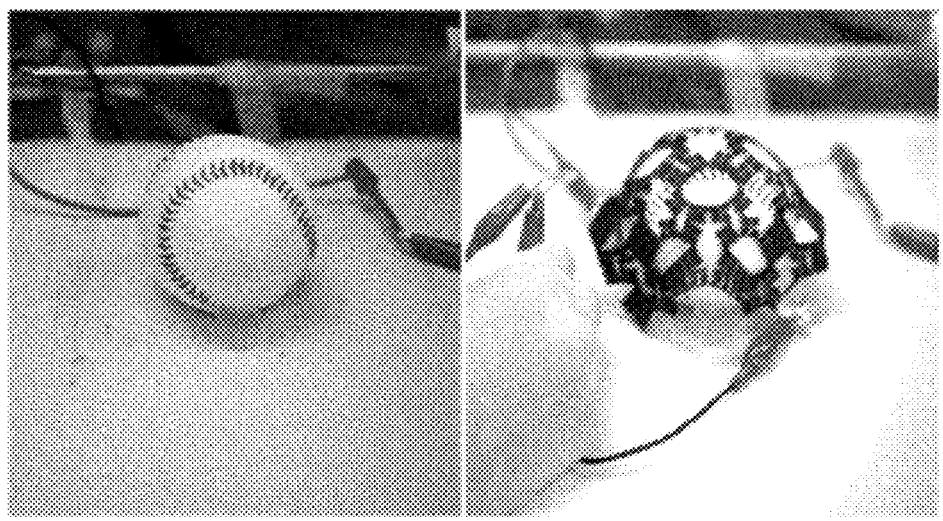
FIG. 10 is a photograph showing that a material manufactured according to Example 2, having electric conductivity, and in an active state maintains electric conductivity even when the material has a hemispherical 3D shape by being supported by a baseball.
Figure 11:
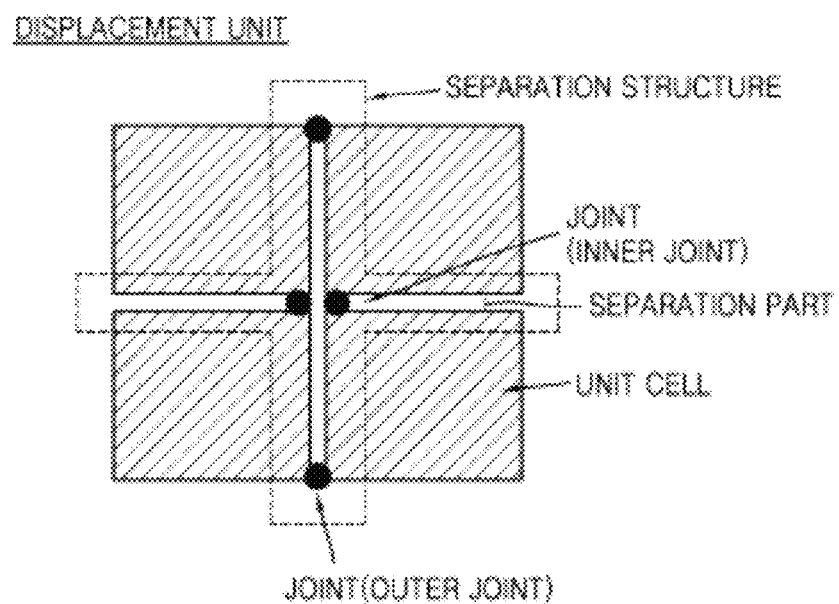
FIG. 11 is a conceptual diagram for describing a name of each part in an example where a displacement unit included in a shape changeable material according to an embodiment of the present disclosure has a quadrangular external shape and m=4.

Further, it was experimented whether the electrode in Example 2 maintained electric conductivity even in a curved surface, and the results are shown in FIG. 10. Referring to FIG. 10, when a commercially available baseball was fixed and the shape changeable electrode was placed on one surface of the spherical curved surface, it is confirmed that the shape changeable electrode generated a space between appropriate unit cells, which may be closely adhered to the spherical curved surface, and thus, had an active state in the form of being closely adhered to the spherical curved surface. Further, as a result of performing an electric conductivity test by using an electric bulb while the electrode was closely adhered to the baseball, it is confirmed that the bulb was lit in brightness similar to that in FIG. 9, and that the shape changeable electrode maintained the electric conductivity even in an active state where the electrode was closely adhered to the curved surface.

One or more embodiments of the present disclosure described above provide a shape changeable material and/or an electrode including the shape changeable material, wherein the shape changeable material has various 2-dimensional (2D) inherent shapes as a hierarchical structure of displacement units or a joint pattern is changed. Accordingly, a material that reversibly changes to inherent shapes (shapes in an active state) derived from pre-applied structural characteristics is provided. For example, the shape changeable material may be used as a flexible material or a stretchable material, and by using the shape changeable material as a supporter, an electrode adherable even on a flexible, stretchable, or irregular surface may be provided.

While one or more embodiments have been described with reference to the figures, it will be understood by those of ordinary skill in the art that various changes in to form and details may be made therein without departing from the spirit and scope as defined by the following claims.

The invention claimed is:

1. A shape changeable material having:
   a hierarchical structure comprising a basic displacement unit comprising a basic separation structure and basic unit cells, and
   a higher level displacement unit located inside the basic unit cell and comprising higher level unit cells distinguished from each other by a higher level separation structure;
   wherein a separation structure comprising the basic separation structure and the higher level separation structure comprises joints connecting neighboring unit cells to each other, wherein the joints have a joint pattern in which a joint shape of an outer joint contacting an outer portion of a displacement unit and an inner joint not contacting the outer portion of the displacement unit is alternately repeated; and
   inherent shapes resulting from hierarchical joint patterns included in higher level displacement units and the hierarchical structure, and activated by rotation movement of the basic unit cells and the higher level unit cells and relative location changes between the unit cells.

2. The shape changeable material of claim 1, wherein a (primary) displacement unit to ($n^{th}$) order displacement unit each comprise a separation structure independently having same or different joint patterns, and displacement units of consecutive orders each have an $n^{th}$ order hierarchical structure forming a hierarchical structure corresponding to the hierarchical structure of the basic displacement unit and the higher level displacement unit, wherein n is an integer equal to or higher than 2.

3. The shape changeable material of claim 2, wherein the (primary) displacement unit has a (primary) unit cell structure comprising a (primary) unit cell$_1$ to a (primary) unit cell$_m$ that are m (primary) unit cells distinguished from each other by a (primary) separation structure, wherein m is an integer of 4 or 6;

the (primary) separation structure comprises a (primary) separation part$_1$ to a (primary) separation part$_m$ that are m (primary) separation parts separating neighboring (primary) unit cells from each other, and comprises a (primary) joint$_1$ to a (primary) joint$_m$ that are m (primary) joints provided at one end of each of the (primary) separation parts, connecting neighboring (primary) unit cells to each other, and having the joint pattern, and at least one (primary) unit cell from among the m (primary) unit cells has, as a (secondary) displacement unit, a secondary or more hierarchical structure comprising a (secondary) separation structure having a same separation structure as the (primary) separation structure, and a (secondary) unit cell structure having the same separation structure as the (primary) separation structure.

4. The shape changeable material of claim 3, having an ($n^{th}$) order hierarchical structure comprising a (primary) displacement unit to an ($n^{th}$) order displacement unit, wherein n is an integer equal to or higher than 3, wherein the (primary) separation structure has an alpha-type joint pattern in which the (primary) joint$_1$ to the (primary) joint$_m$ each have a joint shape selected from an outer joint and an inner joint, and neighboring joints in the (primary) separation structure have different joint shapes, the (secondary) separation structure has any one joint shape selected from an alpha-type joint pattern in which the (secondary) joint$_1$ to the (secondary) joint$_m$ have same joint shapes as the (primary) joint$_1$ to the (primary) joint$_m$, and a beta-type joint pattern in which the (secondary) joint$_1$ to the (secondary) joint$_m$ have different joint shapes from the (primary) joint$_1$ to the (primary) joint$_m$, and a (tertiary) separation structure or each of (tertiary) separation structure to ($n^{th}$) order separation structure has any one joint pattern selected from the alpha-type joint pattern and the beta-type joint pattern.

5. The shape changeable material of claim 4, wherein the (primary) displacement unit to ($n^{th}$) displacement unit each have a quadrangular outer line, wherein m is 4.

6. The shape changeable material of claim 1, wherein the unit cells and the joints comprise any one material selected from the group consisting of silicon rubber, polyester resin, hydrogel, a transition metal, carbon fiber, and a combination thereof.

7. The shape changeable material of claim 2, wherein the unit cells and the joints comprise any one material selected from the group consisting of silicon rubber, polyester resin, hydrogel, a transition metal, carbon fiber, and a combination thereof.

8. The shape changeable material of claim 1, wherein each of the joints connecting the neighboring unit cells form a hinge structure.

9. The shape changeable material of claim 2, wherein each of the joints connecting the neighboring unit cells form a hinge structure.

10. A shape changeable electrode comprising:
a supporter that is the shape changeable material according to claim 1; and
an electric conductive coating layer provided on the supporter.

11. The shape changeable electrode of claim 10, wherein the electric conductive coating layer comprises any one selected from the group consisting of an electric conductive metal nano-particle, carbon nano-tube, graphene, electric conductive polymer, and a combination thereof.

* * * * *